United States Patent
Kobayashi et al.

(10) Patent No.: US 10,980,849 B2
(45) Date of Patent: Apr. 20, 2021

(54) BRAIN FUNCTION IMPROVING AGENT

(71) Applicant: MORINAGA MILK INDUSTRY CO., LTD., Tokyo (JP)

(72) Inventors: Yodai Kobayashi, Zama (JP); Tetsuya Kuhara, Zama (JP); Kanetada Shimizu, Zama (JP); Takumi Sato, Zama (JP)

(73) Assignee: MORINAGA MILK INDUSTRY CO., LTD., Tokyo (JP)

(*) Notice: Subject to any disclaimer, the term of this patent is extended or adjusted under 35 U.S.C. 154(b) by 50 days.

(21) Appl. No.: 16/202,274

(22) Filed: Nov. 28, 2018

(65) Prior Publication Data

US 2019/0083549 A1    Mar. 21, 2019

Related U.S. Application Data

(63) Continuation of application No. PCT/JP2017/020173, filed on May 31, 2017.

(30) Foreign Application Priority Data

May 31, 2016    (JP) .............................. JP2016-108944

(51) Int. Cl.
| | | |
|---|---|---|
| *A61K 35/745* | (2015.01) | |
| *A23L 33/135* | (2016.01) | |
| *A61P 25/28* | (2006.01) | |
| *A61P 25/18* | (2006.01) | |
| *C12N 1/20* | (2006.01) | |
| *A61P 25/24* | (2006.01) | |
| *A61K 35/00* | (2006.01) | |

(52) U.S. Cl.
CPC .......... *A61K 35/745* (2013.01); *A23L 33/135* (2016.08); *A61P 25/18* (2018.01); *A61P 25/24* (2018.01); *A61P 25/28* (2018.01); *C12N 1/20* (2013.01); *A61K 2035/115* (2013.01)

(58) Field of Classification Search
CPC ............ A61K 35/745; A61K 2035/115; A23L 33/135; A61P 25/28; A61P 25/18; A61P 25/24; C12N 1/20
USPC ..................................................... 424/93.4
See application file for complete search history.

(56) References Cited

U.S. PATENT DOCUMENTS

| | | | | |
|---|---|---|---|---|
| 2010/0284979 | A1* | 11/2010 | O'Mahony | ............... C12R 1/01 424/93.44 |
| 2012/0171165 | A1* | 7/2012 | Buck | ...................... A61P 29/00 424/93.4 |
| 2012/0171167 | A1 | 7/2012 | Kondo et al. | |
| 2015/0297584 | A1 | 10/2015 | Tsuruoka et al. | |

FOREIGN PATENT DOCUMENTS

| | | | |
|---|---|---|---|
| EP | 2478910 A1 | | 7/2012 |
| JP | WO 2011/114916 | * | 9/2011 |
| JP | 2014-009214 A | | 1/2014 |
| JP | 2014-101324 A | | 6/2014 |
| WO | WO2011/034166 A1 | | 3/2011 |
| WO | WO2014/070016 A2 | | 5/2014 |
| WO | WO 2016/065419 | * | 5/2016 |

OTHER PUBLICATIONS

Bhattacharjee, S., et al., "Alzheimer's disease and the microbiome," Frontiers in Cellular Neuroscience 2013;7:pp. 1-4; Article 153.
Database GNPD [Online] MINTEL: Jan. 29, 2016, anonymous: "Honey Flavoured Stage 3 Milk Powder," XP055643660, retrieved from www.gnpd.com, database accession No. 3751467, pp. 1-4.
Supplementary European Search Report for European Patent App. No. 17806709.6 (dated Dec. 6, 2019).
Savignac, H. M., et al., "Bifidobacteria modulate cognitive processes in an anxious mouse strain," Behavioural Brain Res. 2015;287:59-72.
Wall, R., et al., "Contrasting effects of Bifidobacterium breve NCIMB 702258 and Bifidobacterium breve DPC 6330 on the composition of murine brain fatty acids and gut microbiota," Am. J. Clin. Nutr. 2012;95:1278-1287.
Yurko-Mauro, K., et al., "Beneficial effects of docosahexaenoic acid on cognition in age-related cognitive decline," Alzheimer's & Dementia 2010;6:456-464.
Kontani, M., et al., "Improvement Effects of a New Supplement Containing Arachidonic Acid (ARA) and Docosahexaenoic acid (DHA) for Dementia Symptoms in Aged Dogs," Japanese Journal of Small Animal Practice 2007;26(5):315-320.
TOMOSADA, Y., et al., "Immunoregulatory Effect of Bifidobacteria Strains in Porcine Intestinal Epithelial Cells through modulation Ubiquitin-Editing Enzyme A20 Expression," PLOS One 2013;8(3):e59259: pp. 1-12.

* cited by examiner

*Primary Examiner* — Jennifer M. H. Tichy
(74) *Attorney, Agent, or Firm* — Cermak Nakajima & McGowan LLP; Shelly Guest Cermak

(57) ABSTRACT

A novel agent useful for improving brain function is provided. The active ingredient in this agent is a *Bifidobacterium breve* and/or a *Bifidobacterium breve*-containing cultured material is provided.

4 Claims, No Drawings

Specification includes a Sequence Listing.

SEQUENCE LISTING

<160> NUMBER OF SEQ ID NOS: 1

<210> SEQ ID NO 1
<211> LENGTH: 42
<212> TYPE: PRT
<213> ORGANISM: Homo sapiens

```
<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

BRAIN FUNCTION IMPROVING AGENT

This application is a Continuation of, and claims priority under 35 U.S.C. § 120 to, International Application No. PCT/JP2017/020173, filed May 31, 2017, and claims priority therethrough under 35 U.S.C. § 119 to Japanese Patent Application Nos. 2016-108944, filed May 31, 2016, respectively, the entireties of which are incorporated by reference herein. Also, the Sequence Listing filed electronically herewith is hereby incorporated by reference (File name: 2018-11-28T_216-002_Seq List; File size: 1 KB; Date recorded: Nov. 28, 2018).

BACKGROUND OF THE INVENTION

Field of the Invention

The present technology relates to an agent that can improve the function of the brain.

Brief Description of the Related Art

In humans, brain function, such as learning ability and memory, is gradually reduced with aging, and as a result, amnesia, anxiety disorder, reduced volition, reduced quality of sleeping, and the like, tend to develop and occur easily. Such law of nature, when combined with the onset of dementia, may lead to a serious result which threatens a person's dignity. Currently, studies on prevention and treatment of dementia are being intensively pursued.

The dementia can refer to a condition of a continuous difficulty in daily life due to the inability to make decisions or a rapid reduction in memory, which result from various impairments caused by brain cell death or poor cell function because of various reasons. The most frequent cause of dementia onset is a neurodegenerative disease, resulting in the gradual death of brain nerve cells, and the next most frequent cause is a cerebrovascular dementia. Neurodegenerative diseases can include, for example, Alzheimer's disease, frontotemporal dementia, and dementia with Lewy bodies. Cerebrovascular dementia is caused by brain nerve cell death or a break in the nervous system network triggered by cerebral infarction, cerebral hemorrhage, cerebral arteriosclerosis, and the like.

Alzheimer's disease is a neurodegenerative disease that can result in 50% to 60% of dementia. The neuropathological characteristics of Alzheimer's disease are neurofibrillary degeneration in the cerebral cortex and hippocampus, senile plaque, and enormous nerve cell exfoliation. While neurofibrillary degeneration results from excessive phosphorylation of a tau protein, which is a microtubule-associated protein that forms a fiber inclusion body, senile plaque results from extracellular accumulation of amyloid β-proteins. In Alzheimer's disease, accumulation of amyloid β-protein accelerates neurofibrillary degeneration, and the tau protein undergoing fibrosis inhibits intracellular transport. In addition, the amyloid β-protein itself is cytotoxic, resulting in impairment of synapse function.

Currently, there are no therapeutics which can radically treat Alzheimer's disease, but pharmaceuticals targeting at improvement and suppression of the symptoms have been reported (for example, see JP-A No. 2014-009214 and JP-A No. 2014-101324).

The upcoming increase in the elderly population and hence a substantial increase in the number of patients with dementia will pose significant social problems. Accordingly, studies are currently required on prevention of onset, as well as improvement or suppressed progression of dementias such as Alzheimer's disease via intervention, especially in daily life habits such as diet.

SUMMARY OF INVENTION

Accordingly, it is an aspect of the present technology to provide a novel agent or composition that improves brain function.

Thus, an agent or composition that improves the function of the brain having a *Bifidobacterium breve* and/or a cultured material containing *Bifidobacterium breve* is/are provided. In the agent or composition as described herein, the aforementioned *Bifidobacterium breve* may be *Bifidobacterium breve* MCC1274 (FERM BP-11175) and/or *Bifidobacterium breve* M-16V (BCCM LMG23729).

Also, regarding the agent or composition as described herein that is able to improve brain function, the aforementioned brain function improvement can be prevention, treatment, and/or improvement of symptoms or diseases resulting from one or more reduced brain functions, such as dementia, depression, schizophrenia, and/or delirium.

Also, regarding the agent or composition as described herein, the aforementioned dementia can be Alzheimer's disease, dementia with Lewy bodies, frontotemporal dementia, and/or cerebrovascular dementia.

Also, a pharmaceutical containing the agent that improves brain function as described herein is provided.

This pharmaceutical may contain the aforementioned *Bifidobacterium breve* at $1\times10^6$ to $1\times10^{12}$ CFU/g.

Furthermore, a food and beverage product able to improve brain function containing a *Bifidobacterium breve* and/or a cultured material containing a *Bifidobacterium breve* is also provided.

Moreover, a *Bifidobacterium breve* and/or a cultured material containing *Bifidobacterium breve* for use toward prevention, treatment, and/or improvement of symptoms or diseases resulting from one or more reduced brain functions such as dementia, depression, schizophrenia, and/or delirium is also provided. In this case, the aforementioned *Bifidobacterium breve* may be *Bifidobacterium breve* MCC1274 (FERM BP-11175) and/or *Bifidobacterium breve* M-16V (BCCM LMG23729).

Also, a method for prevention, treatment, and/or improvement of symptoms or diseases resulting from one or more reduced brain functions such as dementia, depression, schizophrenia, and/or delirium including a step of administering a and/or a cultured material containing a *Bifidobacterium breve* to a subject is also provided. In this case, the aforementioned *Bifidobacterium breve* may be *Bifidobacterium breve* MCC1274 (FERM BP-11175) and/or *Bifidobacterium breve* M-16V (BCCM LMG23729).

Furthermore, a method of production of a pharmaceutical containing a *Bifidobacterium breve* and/or a culture material containing *Bifidobacterium breve*, which is formulated to prevent, treat, and/or improve symptoms or diseases resulting from one or more reduced brain functions such as dementia, depression, schizophrenia, and delirium is also provided. Moreover, a method of producing a food or beverage product containing a *Bifidobacterium breve* and/or a cultured material containing *Bifidobacterium breve*, which is formulated to prevent, treat, and/or improve symptoms or diseases resulting from one or more reduced brain functions such as dementia, depression, schizophrenia, and/or delirium is also provided. In this case, the aforementioned *Bifidobacterium breve* may be *Bifidobacterium breve* MCC1274 (FERM BP-11175) and/or *Bifidobacterium breve* M-16V (BCCM LMG23729).

More specifically, the following is provided:

It is an aspect of the present invention to provide a composition for improving brain function comprising an active ingredient of a *Bifidobacterium breve* and/or a cultured material comprising *Bifidobacterium breve*.

It is a further aspect of the present invention to provide the composition as described above, wherein the *Bifidobacte-*

*rium breve* is *Bifidobacterium breve* MCC1274 (FERM BP-11175) and/or *Bifidobacterium breve* M-16V (BCCM LMG23729).

It is a further aspect of the present invention to provide the composition as described above, wherein said improving brain function comprises prevention, treatment, and/or improvement of symptoms or diseases resulting from a reduced brain function selected from the group consisting of dementia, depression, schizophrenia, delirium, and combinations thereof.

It is a further aspect of the present invention to provide the composition as described above, wherein said dementia is selected from the group consisting of Alzheimer's disease, dementia with Lewy bodies, frontotemporal dementia, cerebrovascular dementia, and combinations thereof.

It is a further aspect of the present invention to provide a pharmaceutical comprising the composition as described above.

It is a further aspect of the present invention to provide the pharmaceutical as described above, comprising the *Bifidobacterium breve* at $1 \times 10^6$ to $1 \times 10^{12}$ CFU/g.

It is a further aspect of the present invention to provide a food or beverage product for improving brain function comprising a *Bifidobacterium breve* and/or a cultured material comprising *Bifidobacterium breve*.

It is a further aspect of the present invention to provide a method for prevention, treatment, and/or improvement of symptoms or diseases resulting from a reduced brain function selected from the group consisting of dementia, depression, schizophrenia, delirium and combinations thereof, comprising a step of administering a *Bifidobacterium breve* and/or a cultured material comprising *Bifidobacterium breve* to a subject.

It is a further aspect of the present invention to provide the method as described above, wherein the *Bifidobacterium breve* is *Bifidobacterium breve* MCC1274 (FERM BP-11175) and/or *Bifidobacterium breve* M-16V (BCCM LMG23729).

It is a further aspect of the present invention to provide a method of using a pharmaceutical composition comprising *Bifidobacterium breve* and/or a cultured material comprising *Bifidobacterium breve*, comprising a step of prevention, treatment, and/or improvement of symptoms or diseases resulting from a reduced brain function selected from the group consisting of dementia, depression, schizophrenia, delirium, and combinations thereof.

It is a further aspect of the present invention to provide a method of using a food or beverage product comprising *Bifidobacterium breve* and/or a cultured material comprising *Bifidobacterium breve* comprising prevention, treatment, and/or improvement of symptoms or diseases resulting from a reduced brain function selected from the group consisting of dementia, depression, schizophrenia, delirium, and combinations thereof.

It is a further aspect of the present invention to provide the method as described above, wherein the *Bifidobacterium breve* is *Bifidobacterium breve* MCC1274 (FERM BP-11175) and/or *Bifidobacterium breve* M-16V (BCCM LMG23729).

Hence, a novel agent or composition that can be used for improving brain function is provided, which is not limited to the improvements and effect described herein.

DETAILED DESCRIPTION OF EXEMPLARY EMBODIMENTS

The following describes the exemplary embodiments for implementing the present technology. The embodiments described below are examples of the representative embodiments of the present technology, and are not intended to be limiting.

<1. Brain Function Improving Agent>

An agent or composition that can be used to improve brain function is described, and in which a *Bifidobacterium breve* and/or a cultured material containing *Bifidobacterium breve* serves as an active ingredient.

*Bifidobacterium breve* is a microbial genus belonging to the genus *Bifidobacterium*. *Bifidobacterium breve* is resident in the large intestine mainly of infants, hence it is known to be an infantile *Bifidobacterium* bacterial species similar to *Bifidobacterium longum* subsp. *infantis* and the like.

Recent studies have indicated that the intestine not only serves to digest and absorb food and drink, but also can influence the mental condition, such as mood or stress. The effects of intestinal flora on brain functions are also attracting attention, and probiotics such as *Bifidobacteria*, when ingested, have been reported to have an anti-anxiety effect (See, for example, Sampson T R et al., Cell Host Microbe. 17(5):565-76, 2015, Ait-Belgnaoui, A. et al., Neurogastroenterol Motil 26(4):510-520, 2014).

It has also been reported that when a human ingests a species of microorganism, such as *Lactobacillus helveticus* R0052 or *Bifidobacterium longum* R0175, stress, anxiety, and anger can be improved (Messaoudi, M. et al., British Journal of Nutrition 105:755-764, 2011). It has also been reported that ingestion of *Bifidobacterium longum* raised the hippocampal BDNF level, and thereby possibly preventing anxiety and related diseases (Bercik et al., Gastroenterology 139: 2102-2112, 2010, JP-T No. 2011-517568).

As described above, the reports of improvement in symptoms or disease associated with reduced brain function upon ingestion of probiotics such as *Bifidobacterium* bacteria relate, however, to *Bifidobacterium longum*, which is resident in adult intestines.

On the contrary, the study as described herein focused on infantile *Bifidobacterium* bacteria instead of the bacteria resident in the adult intestine. After an intensive study, it was surprisingly discovered that among the infantile *Bifidobacterium* bacteria, *Bifidobacterium breve* especially is able to demonstrate the effect of improving brain function.

An agent or composition as described herein, in which the active ingredient is a *Bifidobacterium breve* and/or a culture material containing *Bifidobacterium breve*, is extremely useful because it is highly safe and poses no risk of side effects even when administered continuously for a prolonged period. It is also highly safe when combined with other drugs.

The term "improvement" can mean a change to a better condition of a symptom or a disease, prevention or delay of exacerbation of a symptom or a disease, reversion, prevention, or delay of progression of a symptom or a disease, or treatment of a symptom or a disease treatment, and the like. Also, the term "improvement" can include "prevention". The term "prevention" can mean the avoidance of the onset or delay of the onset of a symptom or a disease in an applicable subject, or reduction in the risk of the onset of a symptom or a disease in an applicable subject, and the like.

The agent or composition that is able to improve brain function can specifically be used, for example, in prevention, treatment, and/or improvement of symptoms of dementia, depression, schizophrenia, delirium, amnesia, reduced ability to make decisions or judgements, or to think, reduced cognitive ability (cognitive decline), and dysfunction of intelligence (intellectual disability).

Among these, prevention, treatment, and/or improvement of symptoms or diseases resulting from one or more reduced brain functions such as dementia, depression, schizophrenia, and/or delirium are exemplary uses of the agent or composition as described herein.

Generally, conditions involving dementia are known to include Alzheimer's disease, dementia with Lewy bodies, frontotemporal dementia, cerebrovascular dementia, and the like. The agent or composition as described herein can be used for prevention, treatment, and/or improvement of symptoms or diseases resulting from one or more reduced brain functions such as Alzheimer's disease, dementia with Lewy bodies, frontotemporal dementia, and/or cerebrovascular dementia.

Generally, in a patient having Alzheimer's disease, brain atrophy (atrophy of cerebral cortex and hippocampus, and enlarged ventricle) is observed and the cerebral cortex exhibits a pathological finding called a senile plaque. A major component of this senile plaque is known to be amyloid beta protein, hereinafter referred to also as "Aβ".

While the cause of Alzheimer's disease has not been definitively determined, it is assumed that the major factor is neurotoxicity that occurs during aggregation and accumulation of the Aβ present in the senile plaques formed in the brain, which degenerates the neurofibrils and eventually leads to nerve cell death.

In view of the results of the Examples described below, the agent or composition that can be used to improve brain function as described herein is considered useful especially in Alzheimer's disease, among the aforementioned dementias.

The bacteria belonging to *Bifidobacterium breve* may, for example, be *Bifidobacterium breve* MCC1274 (FERM BP-11175), and *Bifidobacterium breve* M-16V (BCCM LMG23729).

MCC1274 was deposited with National Institute of Advanced Industrial Science and Technology, International Patent Organism Depositary (Tsukuba Central 6, 1-1-1 Higashi, Tsukuba, Ibaraki 305-8566, Japan, (currently IPOD, National Institute of Technology and Evaluation, International Patent Organism Depositary (NITE-IPOD): Room 120, 2-5-8 Kazusakamatari, Kisarazu, Chiba 292-0818 JAPAN)) on Aug. 25, 2009 under the accession number of IPOD FERM BP-11175.

M-16V was deposited with BCCM Coordination Cell, Federal Public Planning Service Policy (231, avenue Louise, 1050 Brussels, Belgium) on Jun. 27, 2006 under the accession number of BCCM LMG23729. This strain is available from Morinaga Milk Industry Co., Ltd.

These bacteria are generally available from the aforementioned storage agencies.

Among these, it is exemplary to use *Bifidobacterium breve* MCC1274 (FERM BP-11175) and/or *Bifidobacterium breve* M-16V (BCCM LMG23729) as the aforementioned *Bifidobacterium breve* because of their favorable effect for inhibiting cell death.

The *Bifidobacterium breve* employed in the present technology can be readily obtained, for example, by culturing the aforementioned bacteria. The method for culture is not particularly limited as long as these bacteria can proliferate, and the culture can be conducted under an appropriate condition suitable to the characteristics of the bacteria.

Specifically, for example, the culture temperature can be 25 to 50° C., or 35 to 42° C. The culture can be conducted under an anaerobic condition, and for example, anaerobic gas, such as carbonic acid gas, can be ventilated into the culture. It is also possible to conduct the culture under a slightly aerobic condition such as static liquid culture.

The medium for culturing *Bifidobacterium breve* employed in the present technology is not particularly limited, and a medium ordinarily used for culturing bacteria belonging to *Bifidobacterium* can be employed.

Thus, as a carbon source, saccharides such as glucose, galactose, lactose, arabinose, mannose, sucrose, starches, starch hydrolysates, and molasses can be used depending on assimilability. As a nitrogen source, ammonium salts or nitrates such as ammonia, ammonium sulfate, ammonium chloride, and ammonium nitrate can be used. As an inorganic salt, sodium chloride, potassium chloride, potassium phosphate, magnesium sulfate, calcium chloride, calcium nitrate, manganese chloride, and ferrous sulfate can be used. It is also possible to use an organic component such as peptone, soybean flour, defatted soybean meal, meat extracts, and yeast extracts.

*Bifidobacterium breve* can be used as a component in a cultured material obtained after the culture as it is, or further diluted or concentrated, or the bacteria can be recovered from the cultured material.

Also, the active ingredient employed is not only *Bifidobacterium breve*, but can also be a cultured material containing *Bifidobacterium breve*. The term "cultured material" can include a culture supernatant.

The agent or composition for improving brain function as described herein may contain, as active ingredients, one or more of a *Bifidobacterium breve* and/or a cultured material containing *Bifidobacterium breve*. It is also possible that the agent or composition as described herein contains only the aforementioned active ingredients, or the aforementioned active ingredients can be admixed or incorporated with any optional components other than the active ingredients.

The aforementioned optional components are not particularly limited, and additives that are conventionally incorporated in pharmaceutical products, for example, the formulation carrier described below, can be incorporated.

<2. Pharmaceutical>

A pharmaceutical containing the agent or composition useful for improving brain function as described herein is also provided. The pharmaceutical can be used for prevention, treatment, and/or improvement of symptoms or diseases resulting from one or more reduced brain functions such as dementia, depression, schizophrenia, and/or delirium. Exemplary pharmaceuticals can include those formulated for treatment of dementia, depression, schizophrenia, delirium, and the like.

For example, pharmaceuticals formulated for the treatment of dementia, specifically, can include those formulated for the treatment of Alzheimer's disease, dementia with Lewy bodies, frontotemporal dementia, and cerebrovascular dementia.

The pharmaceutical as described herein can be prepared by adding the agent or composition as described herein to a known pharmaceutical, or the agent or composition as described herein can be admixed with the raw materials for a pharmaceutical to produce a novel pharmaceutical.

When the agent or composition useful for improving brain function is used as a pharmaceutical, it may be used as it is, or concentrated, or processed into a solid, granular, or powder product.

The pharmaceutical as described herein can be formulated into an appropriate and desired dosage form depending on the administration method, such as oral administration or parenteral administration. While such a dosage form is not limited, when administering orally, formulations including solid formulations such as powder formulations, granule formulations, tablets, troches, capsules; and liquid formulations such as solution formulations, syrups, suspensions, and emulsions can be used. When administering parenterally, formulations such as suppositories, spray formulations, inhalation formulations, ointments, patches, and injection formulations can be used.

The formulation can be implemented appropriately by known methods depending on the chosen dosage form.

When formulating, a formulation carrier can be, for example, appropriately incorporated. It is also possible to use, in addition the agent or composition useful for improving brain function as described herein, components typically employed in formulations such as excipients, pH modifiers, colorants, and taste masking agents. Component(s) that are able to prevent, treat, and/or improve diseases or symptoms which are known or will be found in the future can be used in combination as appropriate depending on the purpose.

The aforementioned formulation carrier may be organic or inorganic, depending on the chosen dosage form.

In a solid formulation, examples of the carriers can include excipients, binders, disintegrants, lubricants, stabilizers, and flavoring agents.

Examples of the aforementioned excipients can include saccharide derivatives such as lactose, sucrose, glucose, mannitol, and sorbitol; starch derivatives such as corn starch, potato starch, α-starch, dextrin, and carboxymethyl starch; cellulose derivatives such as crystalline cellulose, hydroxypropyl cellulose, hydroxypropyl methyl cellulose, carboxymethyl cellulose, and carboxymethyl cellulose calcium; gum arabic; dextran; pullulan; silicate derivatives such as light silicic anhydride, synthetic aluminum silicate, and magnesium aluminometasilicate; phosphate derivatives such as calcium phosphate; carbonate derivatives such as calcium carbonate; and sulfate derivatives such as calcium sulfate.

Examples of the aforementioned binders can include gelatin; polyvinyl pyrrolidone; and Macrogol, in addition to any of the excipients described above.

Examples of the aforementioned disintegrants can include chemically modified starches or cellulose derivatives such as croscarmellose sodium, carboxymethyl starch sodium, and crosslinked polyvinyl pyrrolidone, in addition to any of the excipients described above.

Examples of the aforementioned lubricants can include talc; stearic acid; metal stearates such as calcium stearate and magnesium stearate; colloidal silica; waxes such as veegum and spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acids such as silicic anhydride and silicic hydrate; and starch derivatives.

Examples of the aforementioned stabilizers can include p-hydroxybenzoates such as methyl paraben and propyl paraben; alcohols such as chlorobutanol, benzyl alcohol, and phenylethyl alcohol; benzalkonium chloride; acetic anhydride; and sorbic acid.

Examples of the aforementioned flavoring agents can include sweeteners, acidifiers, and flavors.

Examples of the carriers employed in a liquid formulation for oral administration can include a solvent such as water and flavoring agents.

It is also possible to use the agent or composition as described herein and a pharmaceutical together with a drug that is able to improve brain function, a drug that is able to treat dementia, a drug that is able to treat depression, a drug that is able to treat schizophrenia, a drug that is able to treat delirium, and the like. These drugs can be known or can be discovered in the future.

While the amount of *Bifidobacterium breve* in the pharmaceutical as described herein is not limited particularly, it is preferable that the amount enables an easy ingestion of the daily dose for efficacious improvement of brain function, which can be, for example, $1 \times 10^6$ to $1 \times 10^{12}$ CFU/g. The daily dose of *Bifidobacterium breve* in the pharmaceutical as described herein can be at least $1 \times 10^6$ CFU/kg body weight/day or higher.

CFU stands for colony forming unit.

In the pharmaceutical as described herein, the daily dose may be administered once a day, or divided into three doses per day. The administration route may be, for example, oral, intraperitoneal, intravenous, intramuscular, transmucosal, nasal, and intrarectal. While the administration subject is usually human, mammals other than human, for example, companion animals such as dogs and cats, livestock such as cattle, sheep, and pigs are also included.

<3. Food and Beverage Product>

A food or beverage product containing a *Bifidobacterium breve* and/or a cultured material containing *Bifidobacterium breve* is also provided. The food or beverage product as described herein is useful for prevention, treatment, and/or improvement of symptoms or diseases resulting from one or more reduced brain functions such as dementia, depression, schizophrenia, and/or delirium. Specifically, the food or beverage product as described herein can be, for example, a health food, functional food, patient food, enteral nutrition food, food for specified use, health functional food intended for improvement of brain function, or treatment of dementia, depression, schizophrenia, delirium, and the like, and food for specified health uses, health functional food, and nutritional functional food as described above.

The food and beverage product that is intended for treatment of dementia can be specifically for treatment of, for example, Alzheimer's disease, dementia with Lewy bodies, frontotemporal dementia, and cerebrovascular dementia.

Examples of the food and beverage products, regardless of their forms such as liquids, pastes, solids, and powders, can include tablet confectioneries, liquid diets, and feeds (including for companion animals), as well as flour products, instant foods, processed agricultural products, processed marine products, processed livestock products, milk and dairy products, fats, basic seasonings, composite seasonings or food products, frozen foods, confectioneries, beverages, and other commercial foods.

Examples of the dairy products can include fermented milk, milk-based beverages, lactic acid bacteria beverages, sweetened condensed milk, skim milk powders, sweetened milk powders, formulated milk powders, creams, cheeses, butters, and ice creams.

Examples of the flour products can include breads, macaroni, spaghetti, noodles, cake mixes, deep frying flours, and bread crumbs.

Examples of the instant foods can include instant noodles, cup-contained instant noodles, retort-cooked foods, cooked and canned foods, microwave foods, instant soups or stews, instant miso soups or clear soups, canned soups, freeze-dried foods, and other instant foods.

Examples of the processed agricultural products can include canned agricultural products, canned fruits, jams or marmalades, pickles, boiled beans, agricultural dry foods, and cereals (processed grain products).

Examples of the processed marine products can include canned marine products, fish meat hams and sausages, marine paste products, marine delicacies, and cocked and seasoned "tsukudani" foods.

Examples of the processed livestock products can include canned livestock/paste products and livestock meat hams and sausages.

Examples of the fats can include butters, margarines, and vegetable oils.

Examples of the basic seasonings can include soy sauces, misos, sauces, processed tomato seasonings, fermented seasoning "mirin" products, and vinegars, and examples of the aforementioned composite seasonings or food products can include cooking mixes, curry bases, gravies, dressings, noodle soup bases "mentsuyu", spices, and other composite seasonings.

Examples of the frozen foods can include material frozen foods, half-cooked frozen foods, and cooked frozen foods.

Examples of the confectioneries can include caramels, candies, chewing gums, chocolates, cookies, biscuits, cakes, pies, snacks, crackers, Japanese sweets, rice confectioneries, bean confectioneries, desserts, and other confectioneries.

Examples of the beverages can include carbonated beverages, natural fruit juices, fruit juice beverages, fruit juice-containing soft beverages, fruit pulp beverages, granule-containing fruit beverages, vegetable-based beverages, soy milks, soy milk beverages, coffee beverages, tea beverages, powdered beverages, concentrated beverages, sports beverages, nutritional beverages, alcoholic beverages, and other tasty beverages.

Examples of the other commercial foods can include baby foods, dried seasoning powders "furikake", and dried seasoning powders "ochazukenori".

Among these, the dairy products are a particular example of the food and beverage product as described herein, with the fermented milks being especially exemplary. As a result, the high nutritional value of the dairy products can also be imparted in addition to the improvement in brain function.

As described herein, the act of "indication" can include all actions that make a consumer aware of the aforementioned use, and any expression, which reminds the consumer of, or, which allows the consumer to assume the aforementioned use, regardless of the purpose of the indication, the contents of the indication, or the indicated subjects or media.

The "indication" can be conveyed, for example, in such a manner that the consumer can immediately recognize the aforementioned use, including, for example, assigning, delivering, or a display for the purpose of assigning or delivering. The packaging of the food and beverage product can have a description of the aforementioned use thereon, as well as an activity to display or distribute advertisement materials, price lists, or transaction documents relating to goods having a description of the aforementioned use thereon or to provide such a detailed information also including a description of the aforementioned use therein via an electromagnetic method (such as internet).

Meanwhile, the detail contents of the "indication" can be one which has been authorized by the relevant government, for example, the indication was authorized under various regulations prescribed by the government and was implemented in a manner based on such an authorization. Such indication details can be attached to the advertising materials wherever the goods sold, such as packages, containers, catalogs, pamphlets, and POPs (Point of purchase advertising) as well as other documents.

The "indication" may also be an indication as to the type of food, such as a health food, functional food, patient food, enteral nutrition food, food for specified health use(s), food with health claims, food with function claims, nutritional functional food, and quasi-drugs. Among these, a particular example is a claim authorized by the relevant government's Consumer Affairs Agency, for example, a claim authorized according to a regulation on food for specified health uses, the regulation on food with function claims, or analogous regulations. Other examples more typically can include an indication as a food for specified health uses, an indication as a conditional food for specified health uses, an indication as a food with function claims, an indication as an effect on body structure or function, and a disease risk reduction claim. Among these, typical examples can include an indication as a food for specified health uses (especially health use claim) prescribed under the Ordinance for Enforcement of Health Promotion Act (Ordinance of the Ministry of Health, Labour and Welfare No. 86 dated Apr. 30, 2003), an indication as a food with function indications prescribed under Food Labeling Act (Act No. 70 of 2013), and analogous indications.

The wording for aforementioned claiming is not limited to wording such as "improvement of brain function, treatment of dementia, depression, schizophrenia, and/or delirium", and other wording may be used, as long as the wording indicates the preventing, improving, and/or treating effects on various diseases and symptoms related to a reduced brain function, as a matter of course. Such a wording can be, for example, based on a various use which allows a consumer to recognize the effects such as improvement of brain function, and/or treatment of dementia, depression, schizophrenia, and/or delirium.

EXAMPLES

The present technology is further detailed below based on the following non-limiting Examples.

In Vivo Example (1) Experimental Method

In this experiment, Alzheimer's disease model mice were prepared by the following procedure, and infantile *Bifidobacteria* (*Bifidobacterium breve* MCC1274 (FERM BP-11175) and *Bifidobacterium longum* subsp. *infantis* ATCC15697) were investigated for their ability to improve cognitive function. The day on which administration of a physiological saline (manufactured by Otsuka Pharmaceutical Co., Ltd.), *Bifidobacterium breve* MCC1274 (FERM BP-11175), *Bifidobacterium longum* subsp. *infantis* ATCC15697 at $1 \times 10^9$ CFU were started to the mice was assigned as Day 1, and on Day 3, an amyloid β-protein fragment 1-42 (Amyloid β-Protein (Human, 1-42), Aβ(1-42) (SEQ ID NO: 1): Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala (Trifluoroacetate Form)) (Peptide Institute, Inc., cat. No. 4349-v) was infused to the mice.

Specifically, mice (ddY mouse: Japan SLC, Inc.) were anesthetized by an intraperitoneal administration of Medetomidine Hydrochloride (manufactured by Meiji Seika Pharma Co., Ltd.) at 0.3 mg/kg, Midazolam (manufactured by Sandoz) at 4 mg/kg, and Butorphanol Tartrate (manufactured by Meiji Seika Pharma Co., Ltd.) at 5 mg/kg. After the anesthesia, the hairs of the top of the animal's head were clipped, and the head was fixed on a brain stereotaxic apparatus. The scalp was disinfected using a disinfectant ethanol, and then was incised to expose the cranial bone. A dental drill was used to form a hole in the cranial bone 1 mm lateral (right side) and 0.2 mm posterior to bregma for stainless steel pipe introduction, through which a stainless-steel pipe connected to a silicone tube of 0.5 mm in outer diameter and a microsyringe was introduced vertically into the ventricle to a depth of 2.5 mm.

Aβ(1-42) was dissolved in a phosphate buffered saline (PBS, pH7.4, manufactured by Thermo Fisher Scientific Inc., cat. No. 10010023) to form an Aβ(1-42) solution, 3 μL (200 pmol/3 μL) of which was then infused into the ventricle using a microsyringe pump over a period of 3 minutes to obtain Alzheimer's disease model mice (Alzheimer's disease model mice group).

A pseudo-surgery mice group (PBS infusion group) was provided by infusing 3 μL of PBS into the ventricle using a microsyringe pump over a period of 3 minutes.

After infusion, the stainless-steel pipe was allowed to remain as inserted for 3 minutes and then the stainless-steel pipe was released slowly. Thereafter, the stainless-steel pipe was removed and the cranial hole was closed using a non-absorbable bone marrow hemostatic agent (Nestop (Trade Mark), manufactured by Alfresa Pharma Corporation) and the scalp was sutured. The administration of physiological saline, *Bifidobacterium breve* MCC1274 (FERM BP-11175), *Bifidobacterium longum* subsp. *Infantis*; ATCC15697 was continued until the end of a behavioral test. 12 ddY mice were employed in each group.

Cognitive function was measured by a Y maze test. In this test, a plastic Y-shaped maze (manufactured by UNICOM) having 3 arms trifurcated at an angle of 120 degrees from each other; each arm had a length of 39.5 cm, a floor width of 4.5 cm, and a wall height of 12 cm. After installation of the device, the bottom of the device was adjusted to be lighted at 20 Lux. The test was conducted about 1 hour after the administration of physiological saline, *Bifidobacterium breve* MCC1274 (FERM BP-11175), and *Bifidobacterium longum* subsp. *infantis* ATCC15697. An animal was placed in one of the arms of the Y-shaped maze and allowed to explore arbitrarily inside of the maze for 8 minutes. The order of the arms to which the animal was moved within the measurement period was recorded, and the number of movements into the arms was counted to obtain a total number of entries. Among these, a combination of three different arms selected consecutively was then investigated to obtain the number of spontaneous alternation behaviors. Using the equation (1) shown below, a % spontaneous alternation behavior was calculated.

ATCC15697 was deposited with ATCC, American Type Culture Collection (10801 University Blvd., Manassas, Va., 20110-2209 USA) under the accession number of ATCC15697.

This bacterium can generally be obtained from the archive described above in a distributable state as described in Supporting Information by D. A. Sela et al., PNAS, Dec. 2, 2008, vol. 105, no. 48, pp. 18964-18969 and the like.

Equation 1:

% Spontaneous alternation behavior=[number of spontaneous alternation behaviors/(total number of entries−2)]×100     (1)

(2) Results of Test

The results of this test are indicated in Table 1 shown below.

TABLE 1

|  | Dosed sample | % spontaneous alternation behavior Mean | SD |
|---|---|---|---|
| Pseudo-surgery mouse group (PBS infusion) | Physiological saline | 64.4*[1] | 6.2 |
| Alzheimer's disease model mouse group | Physiological saline | 53.7 | 5.7 |
|  | *Bifidobacterium breve* MCC1274 (FERM BP-11175) | 62.4*[2] | 10.9 |
|  | *Bifidobacterium longum* subsp. *infantis* ATCC15697 | 57.0 | 7.8 |

*[1] $p < 0.05$ when compared with Aβ + physiological saline group
*[2] $p < 0.05$ when compared with Aβ + physiological saline group As shown in Table 1, the ingestion of *Bifidobacterium longum* subsp. *infantis* ATCC15697 did not improve the cognitive function in the Alzheimer's disease model mice, while the ingestion of *Bifidobacterium breve* MCC1274 (FERM BP-11175) resulted in improved cognitive function in the Alzheimer's disease model mice.

In Vitro Example (1) Experimental Method

In this experiment, the effects of *Bifidobacterium breve* on the Aβ-induced death of nerve cells were evaluated. To human neuroblast SH-SY5Y cells, Aβ was added and the % survival of the cells was measured by MTT assay.

Specifically, the following procedure was conducted. 10% Fetal bovine serum-containing Dulbecco's modified eagle medium (DMEM) (manufactured by Thermo Fisher Scientific Inc.) dispensed in a 96-well plate was inoculated with human neuroblast SH-SY5Y cells at a concentration of $4 \times 10^4$ cells/well. After 12 hours, the medium in the Aβ treatment group was exchanged with 100 μl of the medium containing Aβ(1-42) at 1 μM. In the non-treatment group, the medium was exchanged with an Aβ-free medium. In the Aβ treatment group, 10 nl of the culture supernatant of *Bifidobacterium breve* MCC1274 (FERM BP-11175) or *Bifidobacterium breve* M-16V (BCCM LMG23729) was added and the culture was conducted for 24 hours. The culture supernatant of *Bifidobacterium breve* was obtained by adjusting the culture fluid obtained by a static culture for 16 hours at 37° C. in an MRS medium at OD600=1.0 followed by centrifugation at 2,400 g for 20 minutes. The viable cell count after the culture was measured by using CellQuanti-MTT Cell Viability Assay Kit (BioAssay Systems).

(2) Results of Test

The results of this test are indicated in Table 2 shown below.

TABLE 2

| Supplemented sample (culture supernatant) | | % Cell survival Mean | SD |
|---|---|---|---|
| Non-treatment group | None | 100 | 0.8 |
| Aβ treatment group | None | 70.1 | 1.6 |
|  | *Bifidobacterium breve* MCC1274 (FERM BP-11175) | 77.9**[3] | 1.2 |
|  | *Bifidobacterium breve* M-16V (BCCM LMG23729) | 73.6**[4] | 1.7 |

**[3] $p < 0.01$ when compared with Aβ + Non-supplemented sample group
*[4] $p < 0.05$ when compared with Aβ + Non-supplemented sample group As shown in Table 2, a *Bifidobacterium breve* including *Bifidobacterium breve* MCC1274 (FERM BP-11175) and *Bifidobacterium breve* M-16V (BCCM LMG23729) exhibited inhibition of cell death, and a potent inhibition of cell death was observed especially when using *Bifidobacterium breve* MCC1274 (FERM BP-11175).

INDUSTRIAL APPLICABILITY

According to the present technology, a novel agent able to improve brain function can be provided. An agent or composition as described herein with an active ingredient of a *Bifidobacterium breve* and/or a cultured material containing *Bifidobacterium breve*, is extremely useful because it is highly safe and poses fewer side effects even when administered continuously for a prolonged period.

The invention claimed is:

1. A method for prevention, treatment, and/or improvement of symptoms or diseases resulting from reduced brain function in a subject, comprising a step of administering a *Bifidobacterium breve* and/or a cultured material comprising *Bifidobacterium breve* to the subject,
   wherein said reduced brain function is a result of said subject having a condition selected from the group consisting of dementia, depression, schizophrenia, delirium, and combinations thereof, and
   wherein the *Bifidobacterium breve* is *Bifidobacterium breve* MCC1274 (FERM BP-11175).

2. A method of prevention, treatment, and/or improvement of symptoms or diseases resulting from a reduced brain function in a subject, comprising a step of administering a food or beverage product comprising *Bifidobacterium breve* and/or a cultured material comprising *Bifidobacterium breve* to the subject,
   wherein said reduced brain function is a result of said subject having a condition selected from the group consisting of dementia, depression, schizophrenia, delirium, and combinations thereof, and
   wherein the *Bifidobacterium breve* is *Bifidobacterium breve* MCC1274 (FERM BP-11175).

3. The method of claim 1, wherein said dementia is selected from the group consisting of Alzheimer's disease, dementia with Lewy bodies, frontotemporal dementia, cerebrovascular dementia, and combinations thereof.

4. The method of claim 2, wherein said dementia is selected from the group consisting of Alzheimer's disease, dementia with Lewy bodies, frontotemporal dementia, cerebrovascular dementia, and combinations thereof.

* * * * *